United States Patent
Goto et al.

(10) Patent No.: US 9,382,250 B2
(45) Date of Patent: Jul. 5, 2016

(54) METHOD FOR PRODUCING COMPLEX CRYSTAL AND METHOD FOR SCREENING COMPLEX CRYSTAL

(75) Inventors: Akinori Goto, Tochigi (JP); Mamoru Fukuda, Tokyo (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 166 days.

(21) Appl. No.: 14/113,239

(22) PCT Filed: Apr. 20, 2012

(86) PCT No.: PCT/JP2012/060749
§ 371 (c)(1),
(2), (4) Date: Oct. 22, 2013

(87) PCT Pub. No.: WO2012/144613
PCT Pub. Date: Oct. 26, 2012

(65) Prior Publication Data
US 2014/0045824 A1 Feb. 13, 2014

(30) Foreign Application Priority Data

Apr. 22, 2011 (JP) ................. 2011-096472

(51) Int. Cl.
| | | |
|---|---|---|
| C07B 63/00 | (2006.01) | |
| C07D 223/26 | (2006.01) | |
| C07D 473/08 | (2006.01) | |
| C07D 487/04 | (2006.01) | |

(52) U.S. Cl.
CPC .............. *C07D 473/08* (2013.01); *C07B 63/00* (2013.01); *C07D 223/26* (2013.01); *C07D 487/04* (2013.01)

(58) Field of Classification Search
CPC .... C07B 63/00; C07D 223/26; C07D 473/08; C07D 487/04
See application file for complete search history.

(56) References Cited

FOREIGN PATENT DOCUMENTS

| JP | 2006-518713 | 8/2006 |
|---|---|---|
| JP | 2007-507554 | 3/2007 |
| WO | 2004/078161 | 9/2004 |
| WO | 2007/038524 | 4/2007 |
| WO | 2010/013035 | 4/2010 |

OTHER PUBLICATIONS

Winstein, Neighboring Carbon and Hydrogen. VII. Reactivity of Some Alicyclic and Bicyclic Derivatives, J. Am. Chem. Soc., 74, 1952, 1127-1132.*
Braga et al., "Delaing with Crystal Forms (The Kingdom of Seredip?)," Chem. Asian J. 2011, 6, 2214-2223.*
Extended European Search Report issued Nov. 12, 2014 in European Application No. 12774729.3.
Hickey et al., "Performance comparison of a co-crystal of carbamazepine with marketed product", European Journal of Pharmaceutics and Biopharmaceutics, vol. 67, Dec. 2006, pp. 112-119.
Corvis et al., "Lidocaine/$_L$-Menthol Binary System: Cocrystallization versus Solid-State Immiscibility", J. Phys. Chem. B., vol. 114, Apr. 2010, pp. 5420-5426.
Rahman et al., "Physico-mechanical and Stability Evalution of Carbamazepine Cocrystal with Nicotinamide", AAPS PharmSciTech, vol. 12, No. 2, May 2011, pp. 693-704.

* cited by examiner

*Primary Examiner* — Paul A Zucker
*Assistant Examiner* — Mark Luderer
(74) *Attorney, Agent, or Firm* — Wenderoth, Lind & Ponack, L.L.P.

(57) ABSTRACT

The present invention relates to a method for producing a complex crystal composed of two or more different compounds, comprising crystallizing the two or more different compounds under a condition at which menthol is heat melted, and a method for screening a complex crystal. In accordance with the method for producing a complex crystal of the present invention, a complex crystal capable of being used as a drug material can be produced rapidly, simply and efficiently. In addition, in accordance with the method for screening a complex crystal of the present invention, a stable complex crystal can be searched, which is industrially useful.

4 Claims, No Drawings

1
METHOD FOR PRODUCING COMPLEX CRYSTAL AND METHOD FOR SCREENING COMPLEX CRYSTAL

TECHNICAL FIELD

The present invention relates to a novel crystallization method of a complex crystal (crystal of salt or cocrystal). In particular, the present invention relates to a method for producing a complex crystal and a method for screening a complex crystal.

BACKGROUND ART

It is important in the pharmaceutical field to identify an optimum composition, preparation and/or solid state phase. For example, on the occasion of crystallizing an active pharmaceutical ingredient (API) solely, when formed into a pharmaceutical composition, there may be the case where its stability or solubility or the like is not suited. In such a case, it is attempted to improve the stability or solubility or the like by forming a complex of API with other compound and crystallizing it to prepare a complex crystal (crystal of salt or cocrystal).

As a method for forming a complex of an objective compound with other compound and crystallizing it to prepare a complex crystal, a means for forming a salt of the objective compound with other compound and crystallizing it is a first alternative. In addition, there are also present "compounds which are unable to form a salt, such as neutral compounds having no dissociable group", "compounds which even when forming a salt, do not bring about satisfactory improving effects", or "compounds of which physical properties become inappropriate by the formulation of salts". In such a case, a means for forming a cocrystal of the objective compound with other compound is exemplified as a second alternative.

In general, it is difficult to estimate what combination of compounds is suitable for obtaining an appropriate complex crystal. In particular, different from the crystal of salt, as for the cocrystal, it is difficult to estimate even what combination of compounds forms a complex. Under such circumstances, in order to find out an optimum complex crystal, a massive number of combinations of compounds shall be tried. Therefore, a simple and rapid method for screening a complex crystal is required.

As a method for screening a cocrystal, a method for preparing a suspension mixture using a variety of solvents (slurry method) is known (Non-Patent Document 1). In addition, a method for screening a cocrystal by completely dissolving it in a solvent is known (Patent Documents 1 and 2).

CITED REFERENCE

Patent Documents

[Patent Document 1] Japanese Patent Publication JP-A-2006-518713
[Patent Document 2] Japanese Patent Publication JP-A-2009-516705

Non-Patent Document

[Non-Patent Document 1] N. Takata, K. Shiraki, R. Takano, Y. Hayashi, K. Terada, Cocrystal screening of stanolone and mestanolone using slurry crystallization, Cryst. Growth Des., 8, 3032-3037 (2008).

DISCLOSURE OF THE INVENTION

Problems to be Solved by the Invention

According to the slurry method which has been conventionally adopted, it was necessary to subject a cocrystal to screening by preparing specimens using a variety of solvents relative to one pair of combination of compounds. For that reason, in order to verify a large number of combinations of compounds at the same time, a great deal of labor was required. In addition, according to the method for completely dissolving a cocrystal in a solvent as in the method described in Patent Document 1 or 2, it was required to choose a solvent with, high solubility, and its versatility was poor.

In consequence, an object of the present invention is to provide a method for preparing a complex crystal (crystal of salt or cocrystal) simply and efficiently, which method is rich in versatility, and a method which is suitable for screening a complex crystal.

Means for Solving the Problems

The present inventors made extensive and intensive investigations regarding a method capable of preparing a complex crystal (crystal of salt or cocrystal) simply and efficiently, which method is rich in versatility, and a method for screening a complex crystal. As a result, it has been found that by mixing API with other compound and menthol, heat melting the menthol, and then evaporating it, a combination through which a complex crystal is formed simply can be discovered, leading to accomplishment of the present invention.

That is, the present invention includes the following inventions.

1. A method for producing a complex crystal composed of two or more different compounds, comprising crystallizing the two or more different compounds under a condition at which menthol is heat melted.
2. A method for producing a complex crystal, comprising the following steps (i) and (ii):
    (i) a step of preparing a mixture composed of two or more different compounds and menthol, and
    (ii) a step of heat melting the menthol contained in the mixture.
3. A method for screening a complex crystal, comprising the following steps (I) and (II):
    (I) a step of preparing plural mixtures each containing two or more different compounds and menthol, and
    (II) a step of heat melting the menthol contained in the mixture.
4. A method for producing a complex crystal composed of two or more different compounds and water, comprising crystallizing the two or more different compounds under a humidified condition and under a condition at which menthol is heat melted.
5. The method described in any one of 1 to 4 above, comprising a step of subsequently evaporating the heat melted menthol.
6. The method described in any one of 1 to 5 above, wherein the content of each of the two or more different compounds contained in the mixture is an equimolar amount in the mixture.
7. The method described in any one of 1 to 6 above, wherein the complex crystal is a cocrystal.

Effect of the Invention

According to the method of the present invention, it is not necessary to investigate various kinds of solvents relative to one pair of combination as in the slurry method; a complicated operation such as an operation of choosing a solvent with high solubility and achieving complete dissolution as in Patent Document 1 or 2, is not required; it is rich in versatility; it is possible to produce a complex crystal (crystal of salt or cocrystal) easily within a short period of time using a small amount of a sample; and it is possible to find out a lot of combinations of compounds capable of forming a complex crystal.

EMBODIMENTS FOR CARRYING OUT THE INVENTION

In the present description, the "complex crystal" refers to a crystal in which two or more kinds of compounds form a complex in a fixed stoichiometric ratio; and among them, a crystal in which a force acting between the compounds is an ionic bond is referred to as "crystal of salt", whereas a crystal in which a force acting between the compounds is not an ionic bond is referred to as "cocrystal".

In the present description, the "host compound" refers to a compound which is intended to be combined with other compound to form a complex crystal. In the development of drugs, API is corresponding to the host compound. The "guest compound" refers to a compound which is added for the purpose of forming a complex crystal with the host compound. In general, examples of the guest compound include a carboxylic acid, an amide, an amino acid, and the like.

Here, the above-described "carboxylic acid" means a compound having one or more carboxyl groups in a structure thereof. Specifically, examples thereof include formic acid, acetic acid, propionic acid, butyric acid, valeric acid, benzoic acid, sorbic acid, glycolic acid, malic acid, lactic acid, salicylic acid, oxalic acid, malonic acid, succinic acid, glutaric acid, adipic acid, maleic acid, fumaric acid, phthalic acid, isophthalic acid, terephthalic acid, tartaric acid, and the like, and also derivatives thereof.

The above-described "amide" means a compound having an amide structure in a structure thereof. Specifically, examples thereof include acetamide, propionamide, nicotinamide, benzamide, and the like, and also derivatives thereof.

The above-described "amino acid" means a compound having one or more carboxyl groups and one or more amino groups in a structure thereof. Specifically, examples thereof include glycine, leucine, lysine, alanine, arginine, asparagine, aspartic acid, cysteine, glutamine, glutamic acid, histidine, methionine, phenylalanine, tryptophan, and the like, and also enantiomers or derivatives thereof.

The "menthol" as referred to in the present description may be any of l-menthol, d-menthol, or dl-menthol, or it may be a mixture of l-menthol and d-menthol in an arbitrary proportion. From the viewpoint of easiness of availability, l-menthol is preferable.

(Crystallization Method of Complex)

The method for producing a complex crystal (crystal of salt or cocrystal) composed of two or more different compounds (hereinafter also referred to as "host compound and guest compound") according to the present invention is characterized by crystallizing the two or more different compounds under a condition at which menthol is heat melted.

In order to crystallize the host compound and the guest compound under a condition at which menthol is heat melted, all necessary things to do are that the host compound and the guest compound are mixed under a condition at which menthol is heat melted. Specifically, examples thereof include the following methods (a) and (b).

(a) A method in which after mixing the host compound and the guest compound with menthol, the menthol is heat melted under a condition at which the menthol is heat melted, thereby crystallizing a compound composed of the host compound and the guest compound.

(b) A method in which the host compound and the guest compound are mixed with heat melted menthol, thereby crystallizing a compound composed of the host compound and the guest compound.

The method for producing a complex crystal (crystal of salt or cocrystal) composed of two or more different compounds and the method for screening a complex crystal according to the present invention comprise the following steps 1 and 2.

(Step 1) A step of preparing a mixture composed of two or more different compounds and menthol (Step 2) A step of heat melting the menthol contained in the above-described mixture That is, the method for producing a complex crystal according to the present invention includes (i) a step of preparing a mixture composed of two or more different compounds and menthol; and (ii) a step of heat melting the menthol contained in the above-described mixture.

In addition, the method for screening a complex crystal according to the present invention includes (I) a step of preparing plural mixtures each containing two or more different compounds and menthol; and (II) a step of heat melting the menthol contained in the above-described mixture.

Incidentally, in the method for producing a complex crystal composed of two or more different compounds and the method for screening a complex crystal according to the present invention, the mixing order of the two or more different compounds and the menthol is not particularly limited, and the two or more different compounds and the menthol may be mixed at the same time, or after preparing a mixture composed of the two or more different compounds, the menthol may be added to the mixture.

The steps 1 and 2 are hereunder described.

(Step 1) A step of preparing a mixture composed of two or more different compounds and menthol:

The step 1 is a preparation step for crystallization of a complex. Specifically, for example, a host compound and a guest compound are first mixed. An quantitative ratio of the host compound and the guest compound can be properly chosen depending upon the compounds to be used. In the case where it is unclear at what stoichiometric ratio the host compound and the guest compound form a complex crystal, namely in the case of subjecting a complex crystal to screening, it is preferable to use equimolar amounts of the host compound and the guest compound, respectively.

In the step 1, on the occasion of mixing a host compound and a guest compound, in the case where the amount of the mixture composed of the host compound and the guest compound is not more than about 10 g, a mortar can be used. In particular, on the occasion of using the mixture for screening of a crystal, the amount of the mixture may be enough to be not more than 10 mg, and therefore, in that case, it is preferable to use an agate mortar.

Incidentally, when the particle diameters of the host compound and the guest compound are very large, the frequency of contact of the both becomes low. In such a case, on the occasion of mixing, it is preferable to grind the host compound and the guest compound, thereby increasing the contact frequency of the both.

In the method for screening a complex crystal (crystal of salt or cocrystal) according to the present invention, in the case where the host compound is API, it is preferable to use API in a small amount as far as possible, thereby investigating whether or not a complex crystal is formed in combination with the guest compound.

As a specific method, for example, when an experiment is conducted using an instrument such as a 96-well microplate, not only the small amount of API can be treated at the same time, but the powder X-ray diffraction measurement can be conducted at it is. Therefore, a loss of the sample is a little, and the pretreatment is simple.

Subsequently, the mixture composed of a host compound and a guest compound and menthol are mixed. In general, it is preferable that the host compound and the guest compound are weighed and mixed, and the menthol is then added to the mixture fixed amount of which has been weighed, followed by stirring for mixing.

In the step 1, it is possible to properly choose the amount of the menthol which is added to the host compound and the guest compound, and the amount of the menthol is preferably from 20% to 200%, more preferably from 50 to 150%, and still more preferably 100% relative to a total sum of the mass of the host compound and the guest compound in terms of a mass ratio.

(Step 2) A step of heat melting the menthol contained in the above-described mixture:

The step 2 is a step of heat melting the menthol contained in the mixture composed of a host compound and a guest compound and menthol in the step 1, thereby obtaining a complex crystal composed of the host compound and the guest compound.

It is preferable to properly alter a heating temperature at which the menthol is heat melted depending upon the kinds of the host compound and the guest compound, and in the case where the both compounds do not cause a physical or chemical change upon heating, the heating temperature is preferably from 80 to 100° C.

In the case where there is a possibility that the host compound or guest compound causes a change upon heating, it is preferable to verify the stability against heat in advance.

On the occasion of heat melting the menthol, by conducing heating under a humidified condition, a crystal of complex (hydrate) composed of the two or more different compounds and water can be produced. For example, it is possible to find out a crystal of hydrate by conducting heating in an atmosphere at 80° C. and 90% RH.

The terms "under a humidified condition" as referred to in the present description mean an environmental condition of high relative humidity under a heating condition necessary for the removal of menthol, which is made using an apparatus capable of conducting heating while undergoing humidity control, such as a thermo-hygrostat.

As for the humidified condition, the relative humidity at a temperature for heating is preferably in the range of from 60 to 100%, and more preferably in the range of from 70 to 95%. Incidentally, since it may be considered that the relative humidity at which a hydrate is formed varies depending upon the objective compounds (the host compound and the guest compound), it is preferable to properly adjust the relative humidity. Specifically, for example, the humidified condition refers to an environmental condition such as an atmosphere at 80° C. and 90% RH.

Whether or not the host compound and the guest compound have formed a complex crystal (crystal of salt or cocrystal) can be decided by carrying out the powder X-ray diffraction measurement or thermal analysis.

In the case where whether or not the host compound and the guest compound have formed a complex crystal is decided by means of the powder X-ray diffraction measurement, a diffraction peak of the host compound or guest compound is compared with a diffraction peak in the case where a complex crystal (crystal of salt or cocrystal) is formed.

The case where a diffraction peak is observed at a location where the diffraction peak of the host compound or guest compound is not present indicates that a new crystal structure is formed. Therefore, there is a possibility that a complex crystal (crystal of salt or cocrystal) composed of the host compound and the guest compound is formed.

In the case where whether or not the host compound and the guest compound have formed a complex crystal is decided by means of the thermal analysis, if another melting point other than the melting point of the host compound or guest compound is observed, there is a possibility that a complex crystal (crystal of salt or cocrystal) composed of the host compound and the guest compound is formed.

However, in the case where whether or not the host compound and the guest compound have formed a complex crystal is decided by carrying out the powder X-ray diffraction measurement or thermal analysis, it is preferable to take crystal polymorphs or pseudopolymorphs of the host compound and of the guest compound into consideration, too.

Incidentally, in the formation of a complex crystal (crystal of salt or cocrystal), a ratio of the host compound to the guest compound does not always become 1:1 in terms of a stoichiometric ratio. But, there is a possibility that the crystal is formed in a variety of ratios such as 2:1 or 3:1.

At that time, even in the case of combination which forms a crystal composed of the host compound and the guest compound in a ratio of 2:1, the complex crystal is formed, and the excess of the guest compound merely remains as a mixture. Therefore, by subtracting a diffraction peak derived from the host compound or guest compound, a peak derived from the complex crystal (crystal of salt or cocrystal) can be confirmed.

In addition, at the same time of confirming whether or not the host compound and the guest compound have formed a complex crystal, it is preferable to confirm that the used compounds are not decomposed by confirming a purity of the complex crystal.

In the method for producing a complex crystal and the method for screening a complex crystal according to the present invention, the heat melted menthol can be evaporated by further conducting heating. It is preferable to properly alter a heating temperature at which the menthol is evaporated depending upon the kinds of the host compound and the guest compound, and it can be conducted at the same temperature as the temperature of heat melting.

EXAMPLES

The present invention is hereunder described by reference to specific Examples, but it should not be construed that the present invention is limited thereto.

Example 1

Theophylline and a guest compound shown in Table 1 in an equimolar amount to theophylline were weighed and mixed using an agate mortar. At that time, particles having a large size to an extent that they could be distinguished through visual inspection were grinded on the agate mortar. 10 mg of this mixed powder was weighed and put into a test tube, to which was then added 10 mg of 1-menthol which had been grinded using an agate mortar, followed by vigorously stirring for one minute using a vortex mixer. Thereafter, the obtained mixed powder of theophylline, the guest compound, and 1-menthol was heated for 4 hours in an oven at 80° C., and the obtained solid was subjected to powder X-ray diffraction measurement and thermal analysis. The results are shown in Table 2.

Comparative Example 1-1

3 mg (0.0167 mmoles) of theophylline and a guest compound shown in Table 1 in an equimolar amount (0.0167 mmoles) to theophylline were weighed and put into a glass container, to which was then added 60 μL of water. These were shaken at room temperature for 7 days, and the obtained residues were subjected to powder X-ray diffraction measurement. A summary of the results is shown in Table 2, and the detailed results are shown in Table 3.

Comparative Example 1-2

3 mg (0.0167 mmoles) of theophylline and a guest compound shown in Table I in an equimolar amount (0.0167 mmoles) to theophylline were weighed and put into a glass container, to which was then added 60 μL of ethanol. These were shaken at room temperature for 7 days, and the obtained residues were subjected to powder X-ray diffraction measurement. A summary of the results is shown in Table 2, and the detailed results are shown in Table 3.

Comparative Example 1-3

3 mg (0.0167 mmoles) of theophylline and a guest compound shown in Table 1 in an equimolar amount (0.0167 mmoles) to theophylline were weighed and put into a glass container, to which was then added 60 μL of tetrahydrofuran. This was shaken at room temperature for 7 days, and the obtained residues were subjected to powder X-ray diffraction measurement. A summary of the results is shown in Table 2, and the detailed results are shown in Table 3.

Comparative Example 1-4

3 mg (0.0167 mmoles) of theophylline and a guest compound shown in Table 1 in an equimolar amount (0.0167 mmoles) to theophylline were weighed and put into a glass container, to which was then added 60 μL of toluene. These were shaken at room temperature for 7 days, and the obtained residues were subjected to powder X-ray diffraction measurement. A summary of the results is shown in Table 2, and the detailed results are shown in Table 3.

Comparative Example 1-5

3 mg (0.0167 mmoles) of theophylline and a guest compound shown in Table 1 in an equimolar amount (0.0167 mmoles) to theophylline were weighed and put into a glass container, to which was then added 60 μL of ethyl acetate. These were shaken at room temperature for 7 days, and the obtained residues were subjected to powder X-ray diffraction measurement. A summary of the results is shown in Table 2, and the detailed results are shown in Table 3.

Comparative Example 1-6

3 mg (0.0167 mmoles) of theophylline and a guest compound shown in Table 1 in an equimolar amount (0.0167 mmoles) to theophylline were weighed and put into a glass container, to which was then added 60 μL of acetone. These were shaken at room temperature for 7 days, and the obtained residues were subjected to powder X-ray diffraction measurement. A summary of the results is shown in Table 2, and the detailed results are shown in Table 3.

Comparative Example 2

3 mg (0.0167 mmoles) of theophylline and a guest compound shown in Table 1 in an equimolar amount (0.0167 mmoles) to theophylline were weighed and mixed using an agate mortar. At that time, particles having a large size to an extent that they could be distinguished through visual inspection were grinded on the agate mortar. The obtained solids were subjected to powder X-ray diffraction measurement and thermal analysis. The results are shown in Table 2.

Comparative Example 3

3 mg (0.0167 mmoles) of theophylline and a guest compound shown in Table 1 in an equimolar amount (0.0167 mmoles) to theophylline were weighed and mixed using an agate mortar. At that time, particles having a large size to an extent that they could be distinguished through visual inspection were grinded on the agate mortar. 10 mg of this mixed powder was weighed and put into a test tube, followed by heating for 4 hours in an oven at 80° C. The obtained solid was subjected to powder X-ray diffraction measurement and thermal analysis. The results are shown in Table 2.

TABLE 1

Benzoic acid
Sorbic acid
Oxalic acid
Maleic acid
Glutaric acid
Citric acid
Nicotinamide
Saccharin
Benzamide
Glycine
L-Leucine
L(+)-Arginine
Ethanedisulfonic acid

TABLE 2

| Guest compound | Example 1 | Comparative Example 1* | Comparative Example 2 | Comparative Example 3 |
| --- | --- | --- | --- | --- |
| Benzoic acid | A | C | C | B |
| Sorbic acid | B | A | C | B |
| Oxalic acid | B | A | B | C |
| Maleic acid | A | A | C | B |
| Glutaric acid | A | C | C | B |
| Citric acid | A | A | C | B |
| Nicotinamide | A | A | C | C |
| Saccharin | A | A | C | C |
| Benzamide | A | A | C | C |
| Glycine | C | C | C | C |
| L-Leucine | C | C | C | C |
| L(+)-Arginine | C | A | C | C |
| Ethanedisulfonic acid | A | A | A | A |

A: A cocrystal was completely formed.
B: A mixture of a cocrystal and the host compound or guest compound was formed.
C: A cocrystal was not formed (a mixture of the host compound and the guest compound was formed).
*In any one of Comparative Examples 1-1 to 1-6, a sample in which a cocrystal was formed was evaluated as "A".

TABLE 3

| Guest compound | Comparative Example 1-1 | Comparative Example 1-2 | Comparative Example 1-3 | Comparative Example 1-4 | Comparative Example 1-5 | Comparative Example 1-6 |
|---|---|---|---|---|---|---|
| Benzoic acid | C | C | C | C | C | C |
| Sorbic acid | C | C | C | A | A | C |
| Oxalic acid | C | C | A | C | A | A |
| Maleic acid | C | C | C | A | A | C |
| Glutaric acid | C | C | C | C | C | C |
| Citric acid | C | C | C | C | A | C |
| Nicotinamide | C | B | B | A | A | A |
| Saccharin | C | A | C | C | A | C |
| Benzamide | A | C | C | C | C | C |
| Glycine | C | C | C | C | C | C |
| L-Leucine | C | C | C | C | C | C |
| L(+)-Arginine | A | C | C | C | C | C |
| Ethanedisulfonic acid | C | A | A | A | A | A |

A: A cocrystal was completely formed.
B: A mixture of a cocrystal and the host compound or guest compound was formed.
C: A cocrystal was not formed (a mixture of the host compound and the guest compound was formed).

As shown in Table 2, as compared with the slurry method (Comparative Examples 1-1 to 1-6), the co-grinding method (Comparative Example 2), and the heating method (Comparative Example 3), which methods are the conventional cocrystallization methods, in Example 1, the cocrystal was formed at the highest probability. Incidentally, though a cocrystal of theophylline and L(+)-arginine could be found out in Comparative Example 1-1, it could not be found out in Example 1.

Example 2

Carbamazepine and a guest compound shown in Table 4 in an equimolar amount to carbamazepine were weighed and mixed using an agate mortar. At that time, particles having a large size to an extent that they could be distinguished through visual inspection were grinded on the agate mortar. 10 mg of these mixed powders were weighed and put into a test tube, to which was then added 10 mg of 1-menthol which had been grinded using an agate mortar, followed by vigorously stirring for one minute using a vortex mixer. Thereafter, the obtained mixed powder of carbamazepine, the guest compound, and 1-menthol was heated for 10 hours in an oven at 80° C., and the obtained solids were subjected to powder X-ray diffraction measurement and thermal analysis. The results are shown in Table 5.

Comparative Example 4-1

3 mg (0.0127 mmoles) of carbamazepine and a guest compound shown in Table 4 in an equimolar amount (0.0127 mmoles) to carbamazepine were weighed and put into a glass container, to which was then added 60 μL of water. These were shaken at room temperature for 7 days, and the obtained residues were subjected to powder X-ray diffraction measurement. A summary of the results is shown in Table 5, and the detailed results are shown in Table 6.

Comparative Example 4-2

3 mg (0.0127 mmoles) of carbamazepine and a guest compound shown in Table 4 in an equimolar amount (0.0127 mmoles) to carbamazepine were weighed and put into a glass container, to which was then added 60 μL of ethanol. These were shaken at room temperature for 7 days, and the obtained residues were subjected to powder X-ray diffraction measurement. A summary of the results is shown in Table 5, and the detailed results are shown in Table 6.

Comparative Example 4-3

3 mg (0.0127 mmoles) of carbamazepine and a guest compound shown in Table 4 in an equimolar amount (0.0127 mmoles) to carbamazepine were weighed and put into a glass container, to which was then added 60 μL of tetrahydrofuran. These were shaken at room temperature for 7 days, and the obtained residues were subjected to powder X-ray diffraction measurement. A summary of the results is shown in Table 5, and the detailed results are shown in Table 6.

Comparative Example 4-4

3 mg (0.0127 mmoles) of carbamazepine and a guest compound shown in Table 4 in an equimolar amount (0.0127 mmoles) to carbamazepine were weighed and put into a glass container, to which was then added 60 μL of toluene. These were shaken at room temperature for 7 days, and the obtained residues were subjected to powder X-ray diffraction measurement. A summary of the results is shown in Table 5, and the detailed results are shown in Table 6.

Comparative Example 4-5

3 mg (0.0127 mmoles) of carbamazepine and a guest compound shown in Table 4 in an equimolar amount (0.0127 mmoles) to carbamazepine were weighed and put into a glass container, to which was then added 60 μL of ethyl acetate. These were shaken at room temperature for 7 days, and the obtained residues were subjected to powder X-ray diffraction measurement. A summary of the results is shown in Table 5, and the detailed results are shown in Table 6.

Comparative Example 4-6

3 mg (0.0127 mmoles) of carbamazepine and a guest compound shown in Table 4 in an equimolar amount (0.0127 mmoles) to carbamazepine were weighed and put into a glass container, to which was then added 60 μL of acetone. These were shaken at room temperature for 7 days, and the obtained residues were subjected to powder X-ray diffraction measurement. A summary of the results is shown in Table 5, and the detailed results are shown in Table 6.

Comparative Example 5

Carbamazepine and a guest compound shown in Table 4 in an equimolar amount to carbamazepine were weighed and mixed using an agate mortar. At that time, particles having a large size to an extent that they could be distinguished through visual inspection were grinded on the agate mortar. The obtained solids were subjected to powder X-ray diffraction measurement and thermal analysis. The results are shown in Table 5.

Comparative Example 6

Carbamazepine and a guest compound shown in Table 4 in an equimolar amount to carbamazepine were weighed and mixed using an agate mortar. At that time, particles having a large size to an extent that they could be distinguished through visual inspection were grinded on the agate mortar. 10 mg of this mixed powder was weighed and put into a test tube and heated for 4 hours in an oven at 80° C., and the obtained solids were subjected to powder X-ray diffraction measurement and thermal analysis. The results are shown in Table 5.

TABLE 4

Benzoic acid
Sorbic acid
Oxalic acid
Maleic acid
Glutaric acid
Citric acid
Nicotinamide
Saccharin
Benzamide
Glycine
L-Leucine
L(+)-Arginine
Ethanedisulfonic acid
Malonic acid

TABLE 5

| Guest compound | Example 2 | Comparative Example 4* | Comparative Example 5 | Comparative Example 6 |
|---|---|---|---|---|
| Benzoic acid | A | C | C | B |
| Sorbic acid | A | C | C | B |
| Oxalic acid | A | A | C | B |
| Maleic acid | A | A | C | C |
| Glutaric acid | A | C | C | B |
| Citric acid | B | C | C | B |
| Nicotinamide | A | A | C | B |
| Saccharin | A | A | C | C |
| Benzamide | A | A | C | B |
| Glycine | C | C | C | C |
| L-Leucine | C | C | C | C |
| L(+)-Arginine | C | C | C | C |
| Ethanedisulfonic acid | A | A | C | B |
| Malonic acid | A | A | C | B |

A: A cocrystal was completely formed.
B: A mixture of a cocrystal and the host compound or guest compound was formed.
C: A cocrystal was not formed (a mixture of the host compound and the guest compound was formed).
*In any one of Comparative Examples 4-1 to 4-6, a sample in which a cocrystal was formed was evaluated as "A".

TABLE 6

| Guest compound | Comparative Example 4-1 | Comparative Example 4-2 | Comparative Example 4-3 | Comparative Example 4-4 | Comparative Example 4-5 | Comparative Example 4-6 |
|---|---|---|---|---|---|---|
| Benzoic acid | C | C | — | C | C | C |
| Sorbic acid | C | C | — | C | C | C |
| Oxalic acid | C | C | — | B | A | C |
| Maleic acid | A | A | A | A | A | C |
| Glutaric acid | C | C | — | C | C | C |
| Citric acid | C | C | — | C | — | C |
| Nicotinamide | C | A | A | A | A | B |
| Saccharin | C | A | — | A | A | B |
| Benzamide | B | A | A | A | A | C |
| Glycine | C | C | — | C | C | C |
| L-Leucine | C | C | — | C | C | C |
| L(+)-Arginine | C | C | — | C | C | C |
| Ethanedisulfonic acid | C | A | A | A | A | A |
| Malonic acid | C | C | — | B | A | C |

A: A cocrystal was completely formed.
B: A mixture of a cocrystal and the host compound or guest compound was formed.
C: A cocrystal was not formed (a mixture of the host compound and the guest compound was formed).
—: A residue was not obtained.

As shown in Table 5, as compared with the slurry method (Comparative Example 4), the mixing and grinding method (Comparative Example 5), and the heating method (Comparative Example 6), which methods are the conventional cocrystallization method, in Example 2, it was possible to find out the cocrystal at the highest probability. When the results of Examples 1 and 2 are considered in combination, it may be considered that the method of adding 1-menthol to the host compound and the guest compound and heating them is one of useful methods as a method for screening a cocrystal.

Example 3

About 30 mg (0.167 mmoles) of theophylline and about 29 mg (0.167 mmoles) of L(+)-arginine were weighed and mixed using an agate mortar. At that time, particles had a large size to an extent that they could be distinguished through visual inspection, and therefore, they were grinded on the agate mortar. 15 mg of this mixed powder was weighed and put into a test tube, to which was then added 15 mg of 1-menthol which had been grinded using an agate mortar, followed by vigorously stirring for one minute using a vortex mixer. Thereafter, the obtained mixture of theophylline, L(+)-arginine, and l-menthol was heated for 6 and 21 hours, respectively in a thermo-hygrostat at 80° C. and 90% RH, and the obtained solids were subjected to powder X-ray diffraction measurement and thermal analysis. The results are shown in Table 7.

Comparative Example 7

About 30 mg (0.167 mmoles) of theophylline and about 29 (0.167 mmoles) of L(+)-arginine were weighed and put into a test tube and mixed using an agate mortar. At that time, particles had a large size to an extent that they could be distinguished through visual inspection, and therefore, they were grinded on the agate mortar. 15 mg of this mixed powder was weighed and put into a test tube and heated for 6 and 21 hours, respectively in a thermo-hygrostat at 80° C. and 90% RH, and the obtained solids were subjected to powder X-ray diffraction measurement and thermal analysis. The results are shown in Table 7.

TABLE 7

| Guest compound | Example 3 | | Comparative Example 7 | |
| --- | --- | --- | --- | --- |
| | Heating for 6 hours | Heating for 21 hours | Heating for 6 hours | Heating for 21 hours |
| L(+)-Arginine | A | A | A | A |

A: A cocrystal was completely formed.
B: A mixture of a cocrystal and the host compound or guest compound was formed.
C: A cocrystal was not formed (a mixture of the host compound and the guest compound was formed).

In Example 3, from the results of the powder X-ray diffraction measurement and thermal analysis, it became clear that the menthol remained in the sample after heating for 6 hours. On other hand, it could be confirmed that the menthol did not remain in the specimen after heating for 21 hours.

In Example 3 and Comparative Example 7, the obtained powder X-ray diffraction patterns were coincident with that obtained in Comparative Example 1-1. In addition, from the results of the thermal analysis, a weight reduction of about 9% was observed up to 160° C., and it was considered that this weight reduction is derived from crystallization water. Therefore, it may be considered that the cocrystal of theophylline and L(+)-arginine is a hydrate. As a result of calculation, it was revealed that a stoichiometric ratio of theophylline to L(+)-arginine to water was 1:1:1.

In the light of the above, in the methods of the present invention, it may be considered that by conducting heating under a humidified condition, the menthol can be removed, and furthermore, it is possible to find out a hydrate of cocrystal.

INDUSTRIAL APPLICABILITY

In accordance with the method for producing a complex crystal of the present invention, a complex crystal (crystal of salt or cocrystal) capable of being used as a drug material can be produced rapidly, simply and efficiently. In addition, in accordance with the method for screening a complex crystal of the present invention, a stable complex crystal (crystal of salt or cocrystal) can be searched, which is industrially useful.

While the invention has been described in detail and with reference to specific embodiments thereof, it will be apparent to one skilled in the art that various changes and modifications can be made therein without departing from the spirit and scope thereof. Incidentally, the present application is based on a Japanese patent application filed on Apr. 22, 2011 (Japanese Patent Application No. 2011-096472), the entirety of which is incorporated by reference.

The invention claimed is:

1. A method for screen the formation of a complex crystal, comprising the following steps (I) to (III):
   (I) a step of preparing a mixture containing two or more different compounds and menthol,
   (II) a step of heat melting the menthol contained in the mixture, and
   (III) a step of screening the mixture for the complex crystal.

2. The method according to claim 1, comprising a step of subsequently evaporating the heat melted menthol.

3. The method according to claim 1, wherein the content of each of the two or more different compounds contained in the mixture is an equimolar amount in the mixture.

4. The method according to claim 1, wherein the complex crystal is a cocrystal.

* * * * *